United States Patent
Zhang et al.

(10) Patent No.: US 9,920,305 B2
(45) Date of Patent: Mar. 20, 2018

(54) REVERSE TRANSCRIPTASE WITH ENHANCED PROPERTIES

(71) Applicant: New England Biolabs, Inc., Ipswich, MA (US)

(72) Inventors: Yinhua Zhang, North Reading, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 14/516,124

(22) Filed: Oct. 16, 2014

(65) Prior Publication Data

US 2015/0104790 A1 Apr. 16, 2015

Related U.S. Application Data

(60) Provisional application No. 61/891,554, filed on Oct. 16, 2013.

(51) Int. Cl.
*C12N 9/12* (2006.01)
*C12Q 1/68* (2018.01)

(52) U.S. Cl.
CPC ......... *C12N 9/1276* (2013.01); *C12Q 1/6844* (2013.01); *C12Y 207/07049* (2013.01)

(58) Field of Classification Search
None
See application file for complete search history.

(56) References Cited

U.S. PATENT DOCUMENTS 6,323,009 B1 * 11/2001 Lasken ................ C12Q 1/6844
435/91.1
8,883,421 B2    11/2014 McReynolds et al.

FOREIGN PATENT DOCUMENTS

| WO | WO 2005/028625 | * | 3/2005 |
| WO | 2010/019262 A2 | | 2/2010 |
| WO | 2010/059732 A1 | | 5/2010 |
| WO | WO 2010/059732 | * | 5/2010 |
| WO | 2012/080541 A1 | | 6/2012 |
| WO | 2013/033528 A1 | | 3/2013 |

OTHER PUBLICATIONS

Mohri et al. (Proc. Natl. Acad. Sci. USA. : vol. 90, pp. 25-29, 1993.*
Alvarez et al. (J. Mol Biol., vol. 392, pp. 872-884, 2009.*
Ngo et al. In the Protein Folding Problem and Tertiary Structure Prediction, 1994, Merz et al. (ed.), Birkhauser, Boston, MA, pp. 433 and 492-495.*
Spire et al. (Gene vol. 81, pp. 275-284, 1989.*
Cho et al. (AIDS Res. Hum. Retroviruses 29: 1079-1084 (2013).*
Notomi, et al., Nucleic Acids Research, 28(12):e63, 2000.
Wu, et al., Biochemistry 14(4):789-95, 1975.
Eckert, et al., PCR Methods and Applications, 1:17, 1991.
Mattila, et al., Nucleic Acids Research, 19: 4967, 1991.
Barrioluengo, et al., Biochemical Journal, 436, 599-607, 2011.
International Search Report and Written Opinion for International Application No. PCT/US2014/060876.
Stammers, et al., Crystals of HIV-1 reverse transcriptase diffracting to 2.2 A resolution. J Mol Biol. 1994 242:586-8.
Sarafianos, et al., Structure and function of HIV-1 reverse transcriptase: molecular mechanisms of polymerization and inhibition J. Mol. Biol. 2009 385: 693-713.
Patel, et al., Insights into DNA polymerization mechanisms from structure and function analysis of HIV-1 reverse transcriptase. Biochemistry. 1995 34: 5351-63.
Jacobo-Molina, et al., HIV reverse transcriptase structure-function relationships, Biochemistry 1991 30: 6351-6.
Prasad, et al., Structure-function studies of HIV reverse transcriptase. Ann. NY Acad. Sci. 1990 616: 11-21.
Wrobel, et al., Wrobel et al Analysis of HIV type 1 reverse transcriptase: comparing sequences of viral isolates with mutational data. AIDS Res Hum Retroviruses. 2000 16: 2049-54.
Wrobel, et al., A genetic approach for identifying critical residues in the fingers and palm subdomains of HIV-1 reverse transcriptase. Proc Natl Acad Sci U S A. 1998 95: 638-45.
Kim, et al., Human immunodeficiency virus reverse transcriptase. Functional mutants obtained by random mutagenesis coupled with genetic selection in *Escherichia coli*. J Biol Chem. 1996 271: 4872-8.
Tambuyzer, Compilation and prevalence of mutations associated with resistance to non-nucleoside reverse transcriptase inhibitors. Antivir Ther. 2009;14(1):103-9.

* cited by examiner

*Primary Examiner* — Richard G Hutson
(74) *Attorney, Agent, or Firm* — New England Biolabs, Inc.; Harriet M. Strimpel

(57) ABSTRACT

Compositions and methods are provided for improved reverse transcriptases and their uses in reverse transcription where the improvement may include increased temperature, increased salt, increased activity and/or increased dUTP tolerance.

28 Claims, 5 Drawing Sheets

Reference (SEQ ID NO: 1)
MPISPIETVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDE
DFRKYTAFTIPSINNETPGIRYQYNVLPQGWKGSPAIFQSSMTKILEPFRKQNPDIVIYQYMDDLYVGSDLEIGQHRTKIEELRQHLLRWGLTTPDKKHQKEPPFLWMGYELHPDKWTVQPI
VLPEKDSWTVNDIQKLVGKLNWASQIYPGIKVRQLCKLLRGTKALTEVIPLTEEAELELAENREILKEPVHGVYYDPSKDLIAEIQKEPIVGAETFYDGAANRETKLGKAGYVTLTDTTNQKTELQAIYLALQ
QLTEAVQKITTESIVIWGKTPKFKLPIQKETWETWWTEYWQATWIPEWEFVNTPPLVKLWYQLEKEPIVGAETFYDGAANRETKLGKAGYVTLTDTTNQKTELQAIYLALQ
DSGLEVNIVTDSQYALGIIQAQPDQSESELVNQIIEQLIKKEKVYLAWVPAHKGIGGNEQVDKLVSAGIRKVL V3 (SEQ ID NO: 2)
MPISPIETVPVKLKPGMDGPKVKQWPLTEEKIKALTEICTEMEKEGKISKIGPENPYNTPVFAIKKKDSTKWRKLVDFRELNKRTQDFWEVQLGIPHPAGLKKKKSVTVLDVGDAYFSVPLDK
DFRKYTAFTIPSINNETPGIRYQYNVLPQGWKGSPAIFQSSMTKILEPFRKQNPEIVIYQYMDDLYVGSDLEIGQHRTKIEELREHLLKWGFTTPDKKHQKEPPFLWMGYELHPDKWTVQPIQ
LPEKDSWTVNDIQKLVGKLNWASQIYPGIKVKQLCKLLRGAKALTDVVPLTEEAELELAENREILKEPVHGVYYDPSKDLIAEIQKQGQGQWTYQIYQEPFKNLKTGKYAKMRSAHTNDVKQ
LTEVVQKIATESIVIWGKTPKFRLPIQKETWETWWTEYWQATWIPEWEFVNTPPLVKLWYQLETEPIVGAETFYDGAANRETKLGKAGYVTDRGRQKVVSLTETTNQKTELQAILQALQD
SGSEVNIVTDSQYALGIIQAQPDKSESELVNQIIEQLIKKEKVYLSWVPAHKGIGGNEQVDKLVSSGIRKVL P05959.3 (SEQ ID NO:3)
FPISPIETVPVPVKLKPGMDGPKVKQWPLTEEKIKALVEICTEMEKEGKISKIGPENPYNTPVFAIKKKDSTKWRKLVDFRELNKRTQDFWEVQLGIPHPAGLKKKKSVTVLDVGDAYFSVPLDKE
FRKYTAFTIPSINNETPRIRYQYNVLPQGWKGSPAIFQSSMTKILEPFKKQNPEIVIYQYMDDLYVGSDLEIGQHRIKIEELREHLLKWGFTTPDKKHQKEPPFLWMGYELHPDKWTVQPIVLP
EKDSWTVNDIQKLVGKLNWASQIYAGIKVKQLCKLLRGTKALTEVVQLTKEAELELAENREILKEPVHGVYYDPSKDLIAEIQKQGQGQWTYQIYQEPFKNLKTGKYARMRGAHTNDVKQL
TEAVQKVATESIVIWGKTPKFKLPIQKETWEAWWTEYWQATWIPEWEFVNTPPLVKLWYQLEKEPIIGAETFYDGAANRETKLGKAGYVTDRGRQKVVSLTDTTNQKTELQAIHLALQD
SGLEVNIVTDSQYALGIIQAQPDKSESELVSQIIEELIKKEKVYLAWVPAHKGIGGNEQVDRLVSTGIRKVL Q91080.3 (SEQ ID NO:4)
FPISPIETVPVKLKPGMDGPKVKQWPLTTEKIEALREICTEMEKEGKISRIGPENPYNTPIFAIKKKDSTKWRKLVDFRELNKRTQDFWEVQLGIPHPAGLKQKKSVTVLDVGDAYFSCPLDKDF
RKYTAFTIPSINNETPGIRYQYNVLPQGWKGSPAIFQSTMTKILEPFREKHPEIIYQYMDDLYVGSDLELAQHREAVEDLRDHLLKWGFTTPDKKHQKEPPFLWMGYELHPDKWTVQPIKLP
EKDVWTVNDIQKLVGKLNWASQIYPGIRVKQLCKLIRGTKALTEVVNFTEEAELELAENREILKEPLHGVYYDPGKELVAEIQKQGQGQWTYQIYQELHKNLKTGKYAKMRSAHTNDIKQLV
EVVRKVATESIVIWGKTPKFRLPVQKEVWEAWWTDHWQATWIPEWEFVNTPPLVKLWYQLETEPISGAETFYDGAANRETKLGKAGFVTDRGRQKVVSIADTTNQKAELQAILMALQE
SGRDVNIVTDSQYAMGIIHSQPDKSESELVSQIIEELIKKERVYLSWVPAHKGIGGNEQVDKLVSSGIRKIL Q8AII1.4 (SEQ ID NO:5)
FPISPIEVVKVQLKEGMDGPKVKQWPLSKEKIEALTEICKTLEKEGKISAVGPENPYNTPIFAIKKKDTSKWRKLVDFRELNKRTQDFWELQLGIPHPAGLRKRNMVTVLDVGDAYFSIPLDPD
FRKYTAFTIPSLNNNTPGKRFQYNVLPQGWKGSPAIFQSSMTKILDPFRKEHPDVDIYQYMDDLYIGSDLNEEEHRKLIKLRQHLLTWGLETPDKYQEKPPFMWMGYELHPNKWTVQNI
TLPEEQWTVNHIQKLVGKLNWASQIYKFLLPVSKETWSQWWTDYWQVTWVPEWEFINTPPLIRLWYNLLSDPIPEAETFYDGAANRDSKKGRAGYVTNRGRYRSKDLENTTNQQAELWAVDLALK
QLAGLIQKIGNESIIIWGIVPKFLLPVSKETWSQWWTDYWQVTWVPEWEFINTPPLIRLWYNLLSDPIPEAETFYDGAANRDSKKGRAGYVTNRGRYRSKDLENTTNQQAELWAVDLALK
DSGAQVNIVTDSQYMGVLQGLPDQSDSPIVEQIIQKLTQKTAIYLAWVPAHKGIGGNEEVDKLVSKNIRKIL SEQ ID NO:6
PISPIETVPVKLKPGMDGPKVKQWPLTEEKIKALTEICTEMEKEGKISKIGPENPYNTPVFAIKKKDSTKWRKLVDFRELNKRTQDFWEVQLGIPHPAGLKKKKSVTVLDVGDAYFSVPLDKD
FRKYTAFTIPSINNETPGIRYQYNVLPQGWKGSPAIFQSSMTKILEPFRKQNPEIVIYQYMDDLYVGSDLEIGQHRTKIEELREHLLKWGFTTPDKKHQKEPPFLWMGYELHPDKWTVQPIQ
LPEKDSWTVNDIQKLVGKLNWASQIYPGIKVKQLCKLLRGAKALTDVVPLTEEAELELAENREILKEPVHGVYYDPSKDLIAEIQKQGQGQWTYQIYQEPFKNLKTGKYARMRSAHTNDVK
QLTEVVQKIATESIVIWGKTPKFRLPIQKETWETWWTEYWQATWIPEWEFVNTPPLVKLWYQLETEPIVGAETF

FIG. 6

Sequence Alignment Between V3 and its Reference

| | 10 | 20 | 30 | 40 | 50 | 60 | 70 | 80 |
|---|---|---|---|---|---|---|---|---|
| SEQ ID NO:17 Reference | PI SPI | ETVPVKL | KPGMDGPKVKQWPL | TEEKI KAL M EI | CTEMEKEGKI SKI | GPENPYNTPVFAI | KKKDSTKWRKL | VDFREL 81 |
| SEQ ID NO:18 V3 | PI SPI | ETVPVKL | KPGMDGPKVKQWPL | TEEKI KAL T FI | CTEMEKEGKI SKI | GPENPYNTPVFAI | KKKDSTKWRKL | VDFREL 81 |

| | 90 | 100 | 110 | 120 | 130 | 140 | 150 | 160 |
|---|---|---|---|---|---|---|---|---|
| Reference | NKRTQDFWEVQL GI | PHPAGL | KKKKSVTVLDGDAYFSVPLD E | DFRKYTAFTI PSI | NNETPGI | RYQYNVL | PQGWKGSPAI F 161 |
| V3 | NKRTQDFWEVQL GI | PHPAGL | KKKKSVTVLDGDAYFSVPLD K | DFRKYTAFTI PSI | NNETPGI | RYQYNVL | PQGWKGSPAI F 161 |

| | 170 | 180 | 190 | 200 | 210 | 220 | 230 | 240 |
|---|---|---|---|---|---|---|---|---|
| Reference | QSSMTKI | LEPFRKQN F D | VI YQYMDDL | YVGSDLEI | GQHRTKI EELR Q HL | I R WGL T | TPDKKHQKEPPFL | WMGYEL HPDKWT 241 |
| V3 | QSSMTKI | LEPFRKQN R E | VI YQYMDDL | YVGSDLEI | GQHRTKI EELR E HL | L K WGF T | TPDKKHQKEPPFL | WMGYEL HPDKWT 241 |

| | 250 | 260 | 270 | 280 | 290 | 300 | 310 | 320 |
|---|---|---|---|---|---|---|---|---|
| Reference | VQPI M | PEKDSWTVNDI QKL | VGKL NWASQI | YPGI KV | RQL CKLLRG T | VAL TE M PL | TEEAEL EL AENREI | LKEPVHGVYYD 321 |
| V3 | VQPI Q | PEKDSWTVNDI QKL | VGKL NWASQI | YPGI KV | RQL CKLLRG A | VAL T D WPL | TEEAEL EL AENREI | LKEPVHGVYYD 321 |

| | 330 | 340 | 350 | 360 | 370 | 380 | 390 | 400 |
|---|---|---|---|---|---|---|---|---|
| Reference | PSKDLI AEI | QKQGGQWT YQI | YQEPFKNLKTGKYARM R | AHTNDVKQL TE V VQKI | T ESI VI WGKTPKF Q | PI QKETWET 321 |
| V3 | PSKDLI AEI | QKQGGQWT YQI | YQEPFKNLKTGKYARM R | AHTNDVKQL TE M VQKI | A ESI VI WGKTPKF E | PI QKETWET 321 |

| | 410 | 420 | 430 | 440 | 450 | 460 | 470 | 480 |
|---|---|---|---|---|---|---|---|---|
| Reference | WWT EYWQATWI | PEWEFVNTPPL VKL | WYQLE K EPI | VGAETFYVDGAANRETKL | GKAGYVT | RGRQKVV T | T TTNQKTEL Q 481 |
| V3 | WWT EYWQATWI | PEWEFVNTPPL VKL | WYQLE T EPI | VGAETFYVDGAANRETKL | GKAGYVT | RGRQKVV S | T ETTNQKTEL Q 481 |

| | 490 | 500 | 510 | 520 | 530 | 540 | 550 | 560 |
|---|---|---|---|---|---|---|---|---|
| Reference | AI M ALQDS Q | EVNI VTDSQYAL GI | I QAQPD Q | SESEL VNQI I EQLI | KKEKVYL | A WPAHKGI | GGNEQVDKL V A GI | RKVL 561 |
| V3 | AI Q ALQDS G | EVNI VTDSQYAL GI | I QAQPD K | SESEL VNQI I EQLI | KKEKVYL | S WPAHKGI | GGNEQVDKL V S GI | RKVL 561 |

FIG. 7

REVERSE TRANSCRIPTASE WITH ENHANCED PROPERTIES

CROSS REFERENCE

This application claims priority from U.S. Provisional Application No. 61/891,554, filed Oct. 16, 2013, herein incorporated by reference.

BACKGROUND

Reverse transcriptase (RT) is an RNA-dependent DNA polymerase that synthesizes DNA using RNA as a template. It has been an indispensible reagent in molecular biology for the study of RNA, and in molecular diagnostics for determining the identity of an organism based on a specific RNA sequence in conjunction with DNA amplification. Commonly used RTs are from avian myeloblastosis virus (AMV) and Maloney murine leukemia virus (M-MuLV) and their derivatives. Although each of these RTs has advantages in certain applications, they also have limitations. For example, in molecular diagnostics, the primary concerns are sensitivity and reaction speed. Sensitivity requires that the RT be able to generate enough cDNA for a given amplification platform; the reaction speed determines how quickly the required cDNA product is produced.

Loop-mediated isothermal amplification (LAMP) has been recently adapted to molecular diagnostics for many pathogens due to its convenience in detection and high sensitivity. When a RT is included in LAMP (reverse transcription-LAMP, RT-LAMP), it can be efficiently applied to detect RNA targets, and it has been successfully used for the detection of a number of RNA viruses with great sensitivity. In RT-LAMP, it is essential that the RT be able to efficiently synthesize DNA using the target RNA under conditions optimized for DNA amplification by a DNA-dependent DNA polymerase. This is a significant hurdle which substantially impacts RT selection in RT-LAMP, because the optimal reaction conditions for most RTs do not match the optimal reaction conditions for DNA amplification by DNA-dependent DNA polymerases. The RT most typically used in RT-LAMP is from AMV, because it affords reasonable sensitivity and reaction speed.

Polymerase chain reaction (PCR) has been a major player in DNA amplification. Similar to RT-LAMP, by inclusion of a RT in a PCR reaction (RT-PCR), it is possible to detect RNA. Traditionally RT-PCR is performed in two steps: the first step is RT in an optimized buffer and then PCR in a second step in another buffer condition optimized for PCR. Although these two steps can theoretically be combined, finding a single set of reaction conditions suitable for both steps is challenging. A critical issue is to find RTs that are sensitive and fast even under conditions optimized for the amplification step.

In addition, there are several other properties that would be desirable in a RT for use in one-step detection of RNA by either RT-LAMP or RT-PCR or other amplification technologies. These include: sensitivity and reaction time of the RT, tolerance to high salt and to other potential inhibitors that might carry over from previous RNA sample preparation; and enhanced thermal stability. For example, enhanced thermal stability of the RT permits reverse transcription at a higher reaction temperature so as to reduce the secondary structure of RNA and thereby increase the detection sensitivity and speed. Due to the high demand for RT in molecular diagnostics, the convenience of production and storage are also important features. For example, AMV RT is commonly produced in chicken embryos and it is well known that its production has certain limitations.

SUMMARY OF EMBODIMENTS OF THE INVENTION

RTs are here provided with properties that make them particularly suitable for a wide range of applications. One of these, referred to herein as "V3" and having the amino acid sequence of SEQ ID NO:2 in FIG. 6 or SEQ ID NO:18 in FIG. 7, is demonstrated to be superior in various assays over RTs from AMV and M-MuLV.

Accordingly, in one aspect a polypeptide is provided that includes an amino acid sequence at least 90% identical to SEQ ID NO:18 or 95% identical to SEQ ID NO:18. Alternatively, the polypeptide includes an amino acid sequence that is at least 96% identical to the heterodimer small unit of V3 that contains the first 442 amino acids of V3 (SEQ ID NO:6). The polypeptide may be more than 95% identical to SEQ ID NO:18 or SEQ ID NO:6, such as at least 96% identical, at least 96.5% identical, at least 97% identical, at least 97.5% identical, at least 98% identical, at least 98.5% identical, at least 99% identical, at least 99.5% identical, or 100% identical to SEQ ID NO:18. Thus, the sequence may differ from SEQ ID NO:18 or SEQ ID NO:6 at no more than 56 residues, and may differ at fewer (e.g., no more than 23, no more than 22, no more than 21, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, no more than 1, or zero). In addition to the identities described above, the polypeptide or the polypeptide fused to a second peptide or polypeptide may sustain deletions of non-essential sequences of amino acids.

The amino acid sequence included in the polypeptide that is at least 96% (or more, e.g. at least 98%) identical to SEQ ID NO:2 is different from a reference sequence identified in FIG. 6 as SEQ ID NO:1. For example, in FIG. 7, the amino acid sequence may differ from SEQ ID NO:17 (SEQ ID NO:17 is the same as SEQ ID NO:1 but without the Methionine at position 1) at one or more (e.g. at least two, at least five, at least ten, at least fifteen, at least twenty, 21, 22, 23, 24, or 25) positions corresponding to amino acids 35, 122, 177, 206, 211, 214, 245, 277, 286, 291, 293, 356, 359, 371, 376, 390, 431, 460, 468, 471, 483, 491, 512, 534, and 554 of SEQ ID NO:17 in addition to any other differences which may be present.

In addition to the amino acid sequence having the identities or differences described above, the polypeptide may additionally include (e.g. be fused to) non-homologous peptide or polypeptide sequence. Thus, while the polypeptide always includes an amino acid sequence at least 90% identical to SEQ ID NO:2 (e.g. at least 96% or at least 98% identical to SEQ ID NO:2 or SEQ ID NO:18), the polypeptide may optionally include one or more additional sequences, such as a peptide tag to facilitate in vitro purification, or a peptide tag that enhances DNA binding, or a peptide tag that facilitates detection of the polypeptide or its substrate in situ. Examples of such additional peptide or polypeptide sequences include DNA binding domains (for example, Sso7D or Sac7D), affinity binding domains (such as chitin binding domain), and amino acid sequences for detection of the polypeptides such as AGT (SNAP-Tag® New England Biolabs, Ipswich, Mass.).

Similarly, embodiments provide nucleic acids encoding any of these polypeptides. The nucleic acid at least includes the nucleotides encoding the polypeptide, and may include additional nucleotide sequences. For example, the nucleic acid may be a plasmid or other vector facilitating the replication of the nucleic acid in a cell. Alternatively, or in addition, the nucleotides encoding the polypeptide may be associated with a promoter driving expression of the polypeptide in a cell. Embodiments also provide cells containing a nucleic acid encoding any of these polypeptides.

In another aspect, an enzyme preparation may contain any of the polypeptides described above. The enzyme preparations may, for example, be substantially free (i.e. undetectable by gel electrophoresis, chromatography or by PCR amplification) of contaminating nucleic acids. The composition may alternatively or in addition include a detergent, such as a non-ionic detergent, a cationic detergent, an anionic detergent, and/or a zwitterionic detergent. Nonionic detergents, for example, have been reported to stimulate some reverse transcriptases (Wu, et al., *Biochemistry* 14(4): 789-95, 1975). Exemplary nonionic detergents include Polysorbate 20 (also known as "Tween 20"), Triton X-100, and NP40. Exemplary anionic detergents include poly(ethylene glycol) 4-nonylphenyl 3-sulfopropyl ether potassium salt; poly(ethylene glycol) monolaurate; polyoxyethylene(150) dinonylphenyl ether; and nonyl nonoxynol-15 phosphate. Exemplary zwitterionic detergents include 3-(N,N-dimethyltetradecylammonio)propanesulfonate (SB3-14); 3-(4-Heptyl)phenyl-3-hydroxypropyl)dimethylammoniopropanesulfonate (C7BzO); CHAPS (3-[(3-cholamidopropyl) dimethylammonio]-1-propanesulfonate); CHAPSO (3-[(3-cholamidopropyl)dimethylammonio]-2-hydroxy-1-propanesulfonate); 3-(decyldimethylammonio) propanesulfonate inner salt (SB3-10); 3-(dodecyldimethylammonio) propanesulfonate inner salt (SB3-12); 3-(N,N-dimethyloctadecylammonio) propanesulfonate (SB3-18); 3-(N,N-dimethyloctylammonio) propanesulfonate inner salt (SB3-8); 3-(N,N-dimethylpalmitylammonio) propanesulfonate (SB3-16); and 3-[N,N-dimethyl(3-myristoylaminopropyl)ammonio]propanesulfonate (ASB-14). Stabilization reagents include those described in U.S. Pat. No. 8,715,987.

In some embodiments, the enzyme preparation includes potassium chloride, either at a moderate concentration (such as about 50 mM) or a high concentration (such as at least 0.35M). In some embodiments, the enzyme preparation includes potassium chloride at high concentrations of at least 0.4M, or at least 0.45M.

In some embodiments, the composition (enzyme preparation) includes a buffer. The pH of the buffer is optionally alkaline, such as at least pH 8.3, such as between pH 8.3 and pH 9.3.

In some embodiments, the composition (enzyme preparation) includes potassium chloride at a moderate or high concentration as defined herein and is buffered at a pH between pH 8.3 and pH 9.3.

In some embodiments, the composition (enzyme preparation) includes deoxyribonucleotides (e.g. dATP, dCTP, dTTP, and dGTP). In certain embodiments, the composition includes dUTP instead of or in addition to dTTP. One or more of the deoxyribonucleotides can optionally be labeled with a detectable label, such as a fluorophore or a quencher.

In some embodiments, the composition includes RNA, such as synthetic RNA or RNA from a cell (whether obtained directly from a cell or tissue sample, from a biological fluid, from an environmental sample, etc.). For example, the RNA could be the product of two or more RNA molecules ligated together to form a single, unitary RNA molecule, such as by T4 RNA Ligase 1, T4 RNA Ligase 2, or truncated T4 RNA Ligase 2 (New England Biolabs, Ipswich, Mass.). Alternatively, or in addition, the RNA could be coupled to a synthetic RNA adaptor, e.g. by T4 RNA ligase 2, truncated (New England Biolabs, Ipswich, Mass.).

In some embodiments, the composition includes one or more (e.g. at least two, four, six, eight, or more) primers. At least one primer may include a first nucleic acid sequence for hybridizing to a target RNA in a sample. In certain embodiments, at least one primer includes a first nucleic acid sequence for hybridizing to a target RNA in a sample, and a second nucleic acid sequence that does not hybridize to the target RNA but instead encodes information about the target RNA upon amplification of the target RNA. In some embodiments, at least one primer in the composition may be attached to a solid support, such as a bead, useful, for example, in enriching a sample for RNA molecules complementary to the primer. Any of the primers may additionally include a barcode or unique identifying sequence.

In some embodiments, the composition further includes a DNA-dependent DNA polymerase, useful for amplifying the complementary DNA strand resulting from reverse transcription. The DNA-dependent DNA polymerase may be, for example, Bst 2.0 (New England Biolabs, Ipswich, Mass.), Taq polymerase, an archeal polymerase or an archeal polymerase fusion product of two archael polymerases such as Phusion® (Thermo Scientific, Pittsburgh, Pa.) or Q5® (New England Biolabs, Ipswich, Mass.). The molecular ratio of the RT polypeptide to the DNA-dependent DNA polymerase, if present, may be less than 2:1. For example, the molecular ratio of the RT polypeptide to the DNA-dependent DNA polymerase, if present, may be less than 3:2 (such as less than 1:1, less than 0.75:1, less than 0.5:1, less than 0.3:1, less than 0.2:1, or less than 0.1:1).

Embodiments also provide kits useful for reverse transcription of RNA. The kits include any of the RT polypeptides defined herein, in combination with at least one separate component including one or more of the following: a buffer (e.g. as defined herein, optionally buffered at a pH of between pH 8.3 and pH 9.3), a nucleic acid (optionally attached to a solid support), deoxyribonucleotides, potassium chloride (e.g. at moderate or high concentration as defined herein), magnesium sulfate, ammonium sulfate, a nucleic acid binding dye such as SYTO 9® or SYBR® Green (Life Technologies, Grand Island, N.Y.), a DNA-dependent DNA polymerase such as Bst 2.0, Taq polymerase, an archeal polymerase, or an archeal polymerase fusion product (of two archael polymerases such as Phusion or Q5) and a uracil-DNA glycosylase. In one embodiment, the kit includes a RT polypeptide comprising an amino acid sequence that is at least 96% identical to SEQ ID NO:2 (such as at least 98%, or 100% identical to SEQ ID NO:18).

In another aspect, embodiments provide methods for reverse transcribing RNA. The method involves exposing the RNA to any of the RT polypeptides defined herein, or to one of the above-described compositions or kits including at least the RT polypeptide, primers, a buffer, and deoxyribonucleotides and optionally an adapter or plurality of adapters. The adapter(s) may include a barcode and/or a unique identifying sequence that recognizes a sequence source of the RNA. In one embodiment, the RT polypeptide comprises an amino acid sequence that is at least 96% identical to SEQ ID NO:18 (such as at least 98%, or 100% identical to SEQ ID NO:18). The polypeptide reverse transcribes the RNA to produce a complementary strand of DNA. Preferably, the method shows one or more of improved activity, salt tolerance (e.g. to high salt concentrations), thermostability (e.g.

stability to temperatures of at least 60° C.), and/or dUTP tolerance, as compared to a method comprising exposing the same RNA to AMV RT or MuMLV RT under the same conditions. The RNA may be from a crude preparation, or may be purified prior to the exposing step, such as by using a primer attached to a solid support to selectively enrich the sample for a desired subset of RNA molecules.

Embodiments include an additional step of preventing adapter-dimer formation using, for example, the methods described in U.S. patent application Ser. No. 13/383,466.

Embodiments also provide methods of amplifying RNA by reverse transcribing it as described above and exposing the resulting complementary strand of DNA to a DNA-dependent DNA polymerase in the presence of primers, deoxynucleotides, and buffer. The DNA amplification may involve, for example, PCR, or isothermal methods such as LAMP, transcription mediated amplification, or helicase-dependent amplification. In one embodiment, the DNA amplification involves LAMP.

In one aspect, a method is provided for one-step RT-PCR, said method including: (a) mixing an RNA template with a composition comprising a polypeptide according to claim 1 and one or more DNA polymerases; and (b) incubating the mixture under conditions sufficient to amplify a DNA molecule complementary to all or a portion of the RNA template.

BRIEF DESCRIPTION OF THE FIGURES

As shown in FIG. 1, the rate of amplification of RNA using RT-LAMP is significantly improved when the target RNA is reverse transcribed using the variant V3 RT compared with AMV transcriptase across the temperature range of 55° C.-70° C.

As shown in FIG. 2, V3 RT retains activity after 2 minutes pre-incubation at 65° C. prior to addition of RNA substrate, whereas AMV RT has lost most of its activity at 60° C.

Figure 1:
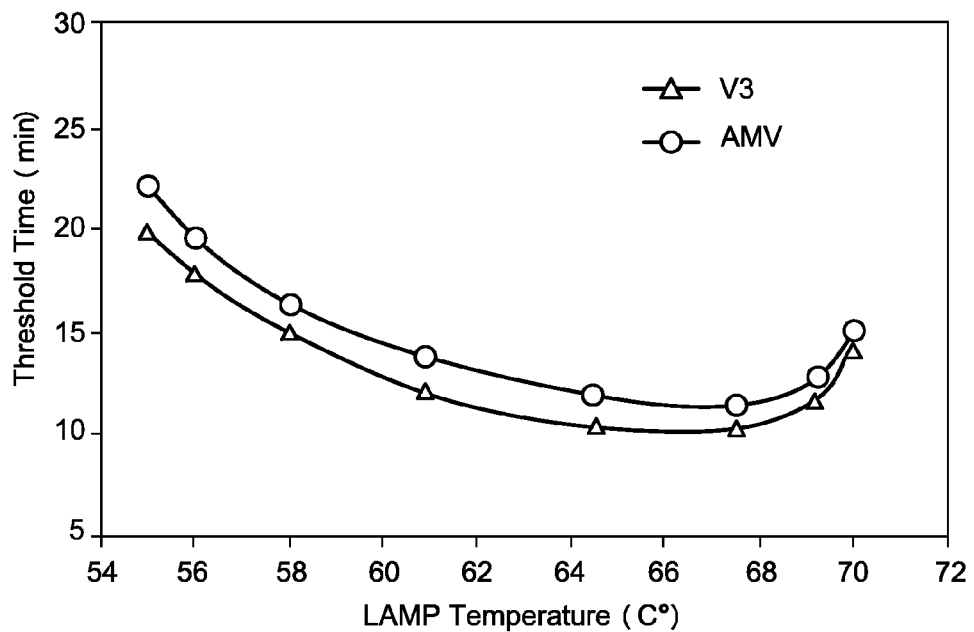
FIG. 1 is a graphical depiction of the relationship of the signal threshold time of LAMP amplification to the temperature of the reaction when using either V3 or AMV RT.

The X-axis shows the number of PCR cycles and the Y-axis shows the recorded fluorescent signal which corresponds to the amount of DNA produced in the PCR tubes. V3 RT (triangle) generated robust qRT-PCR signal at around 20 cycles with both ACTB and B2M primer pairs, while ProtoScript II RT (circle) produced only marginal signal and MMuLV-RT (straight lines) did not produce any signal.

FIG. 6 provides full length sequences of a reference RT (p66; SEQ ID NO:1); V3 (SEQ ID NO:2); and three other variants (SEQ ID NOs:3-5).

FIG. 7 illustrates the differences between V3 (SEQ ID NO:18) and a reference sequence (SEQ ID NO:17) by alignment of their amino acid sequences. The position numbers of mutations provided here for SEQ ID NO:17 and SEQ ID NO:18 differ in number by one amino acid from SEQ ID NO:1 and 2 in FIG. 6 because the initial methionine (M) has not been included in FIG. 7.

DETAILED DESCRIPTION OF EMBODIMENTS

Polypeptides according to embodiments of the invention can reverse transcribe RNA, creating a complementary strand of DNA, under any of a variety of conditions. An exemplary polypeptide according to embodiments is V3 (SEQ ID NO:2). As shown in the examples, V3 demonstrates enhanced activity, salt tolerance (e.g. to high concentrations of KCl of at least 0.35M), thermostability (e.g. to temperatures of at least 60° C.), and/or tolerance for dUTP, compared to other reverse transcriptases.

Embodiments also include 'variant' polypeptides that differ from SEQ ID NO: 1 and/or SEQ ID NO:2 and/or SEQ ID NO:17 and/or SEQ ID NO:18 and/or SEQ ID NO:6 (as defined herein); and polypeptides that include SEQ ID NO:2 or SEQ ID NO:6 or a 'variant' thereof.

In one embodiment, the polypeptides comprise or consist of an amino acid sequence that is at least 96% identical to SEQ ID NO:2 having RT activity under the conditions described herein.

Embodiments of the polypeptides which may be non-naturally occurring, and may include one or more amino acid mutations at the N-terminal end such as for example, one or more mutations at positions 35, 122 and 177 of SEQ ID NO:1. Additionally or alternatively, the polypeptides may include one or more amino acid mutations in a central domain including one or more mutations at position 206, 211, 214, 245, 277, 286, 291 and/or 293 of SEQ ID NO:17. Additionally or alternatively, the polypeptides may include one or more amino acid mutations at the C-terminal end such as for example one or more mutations at positions 356, 359, 371, 376, 390, 431, 460, 468, 471, 483, 512, 534 and 554 of SEQ ID NO:17. In an embodiment, the polypeptide may include one or more mutations from the N-terminal domain and the C-terminal domain or the N-terminal domain and the central domain or the central domain and the C-terminal domain. Alternatively, the polypeptide may contain one or more mutations from the N-terminal domain, the central domain and the C-terminal domain wherein examples of mutations in these domains are provided above.

The polypeptide may be a non-naturally occurring variant of a polypeptide having a sequence defined by SEQ ID NO:3-5 where these variants have at least 96% sequence identity with SEQ ID NO:1 or SEQ ID NO:2 or SEQ ID NO:17 or SEQ ID NO:18, and be synthetic polypeptides having no recognized counterpart in nature.

Moreover, embodiments of the polypeptides have RT activity of the type described above. Preferably, the RT activity is greater for the mutant than for the wild type RT characterized by the amino acid sequence described in SEQ ID NO:1 or SEQ ID NO:17.

The polypeptides may be prepared recombinantly using an expression vector with a promoter upstream of a nucleotide sequence encoding the polypeptide.

An RT reaction may be performed with the polypeptides or compositions described in the summary of embodiments under conditions to allow for reverse transcription and generation of a first and optionally second strand cDNA. The RT reaction can be primed with a random primer, an oligo dT, or an RNA-specific primer.

If desired, the reactions can also include amplification of cDNA, such as by LAMP or PCR. Techniques for performing LAMP are known in the art (see, for example, Notomi, et al., *Nucleic Acids Research*, 28(12):e63, 2000), as are techniques for performing PCR assays (Erlich, *PCR Technology: Principles and Applications for DNA Amplification*, 1989; Innis, et al., *PCR Protocols: A Guide to Methods and Applications*, 1990; Mattila, et al., *Nucleic Acids Research*, 19: 4967, 1991; Eckert, et al., *PCR Methods and Applications*, 1:17, 1991; Wallace, et al., *Ligase Chain Reaction, in Technologies for Detection of DNA Damage and Mutations*, pp. 307-322, 1996). Various guidelines may be used to select appropriate primer sequences and hybridization conditions (see, e.g., Sambrook, et al, *Molecular Cloning: A Laboratory Manual*, 1989; Ausubel, et al., *Short Protocols in Molecular Biology*, 4th edition, 1999; Ausubel, et al., *Current Protocols in Molecular Biology*, 1999-2010).

The variant RTs described herein have at least one improvement over commonly used RTs (AMV and/or M-MuLV and/or the RT encoded by SEQ ID NO:1 or SEQ ID NO:17) under the same reaction conditions with the same substrates and primers etc. that may include any or all of the following:

Enhanced activity: Embodiments of the polypeptides described herein including V3 may be able to perform a RT reaction in a reduced time frame for example at least twice as fast under standard conditions for each enzyme. The enhanced activity includes three times, four times, five times increased activity. The enhanced activity has been observed for polynucleotides of less than 500 base pairs in length.

Thermostability: Because of the enhanced thermostability of the polypeptides described herein, reactions can be performed at a higher temperature than would otherwise be possible otherwise. Embodiments of the polypeptides described herein including V3 may have RT activity that is capable of improved activity at higher temperatures.

The RT polypeptides may be thermostable at a temperature of at least 50° C., at least 55° C., at least 60° C., or at least 65° C. These RTs may be used in RT reactions at temperatures of at least 43° C., at least 45° C., at least 50° C., at least 55° C., at least 60° C., or at least 65° C., such as at a temperature of between 43°-65° C., 45°-65° C., 50°-65° C., 55°-65° C., 60°-65° C., 55° C.-70° C., or 65°-70° C. Performing the reaction at a higher temperature reduces the risk of the template RNA forming secondary structures that may inhibit reverse transcription.

Resistance to Salt: The RT polypeptides may be resistant to salt (e.g. KCl) concentrations at or above 0.35M, such as at least 0.40M or at least 0.45M. Embodiments of the present reverse transcriptases may be active in salt concentrations in the range of 50M-500 mM for example 50 mM, 100 mM, 125 mM, 150 mM, 175 mM, 200 mM, 225 mM, 250 mM, 300 mM or 400 mM salt. The activity of the RT for these polypeptides under the higher salt conditions may be the same or greater over commonly used RTs (AMV and/or M-MuLV and/or the RT encoded by SEQ ID NO:1) under the same reaction conditions with the same substrates and primers etc. Thus, for example, in embodiments in which a salt concentration of less than 0.35M would be optimal for a conventional reverse transcriptase, the polypeptides of the invention allow for the RT to perform an RT reaction at higher salt concentrations of at least 0.35M or higher than would otherwise be possible.

Another advantage of embodiments of the polypeptides may include increased tolerance for dUTP, compared to other reverse transcriptases.

Advantages and implementations of specific embodiments of the invention are described in the figures and examples, which are not intended to limit the invention identified in the accompanying claims. All references cited herein are incorporated by reference.

EXAMPLES

Example 1

Human actin B mRNA was amplified by RT-LAMP using an ActB2 primer set (ACTB2-F3: AGTACCCCATCGAG-CACG (SEQ ID NO:7); ACTB2-B3: AGCCTGGATAG-CAACGTACA (SEQ ID NO:8); ACTB2-FIP: GAGCCA-CACGCAGCTCATTGTATCACCAACTGGGACGACA (SEQ ID NO:9); ACTB2-BIP: CTGAACCCCAAGGC-CAACCGGCTGGGGTGTTGAAGGTC (SEQ ID NO:10); ACTB2-LF: TGTGGTGCCAGATTTTCTCCA (SEQ ID NO:11); ACTB2-LB: CGAGAAGATGACCCAGAT-CATGT (SEQ ID NO:12)). The RT-LAMP reaction was performed in 25 µl with 1× Isothermal Amplification Buffer (20 mM Tris-HCl (pH 8.8, 25° C.), 10 mM $(NH_4)_2SO_4$, 50 mM KCl, 2 mM $MgSO_4$, 0.1% Tween 20 supplemented with 8 mM $MgSO_4$, and 1.4 mM each of dATP, dCTP, dGTP, and dTTP. The primer concentrations were: 0.2 µM ACTB2-F3 or ACTB2-B3, 1.6 µM ACTB2-FIP or ACTB2-BIP and 0.4 µM LF or LB. Each reaction included 5 ng V3 or 0.5 U of AMV RT (New England Biolabs, Ipswich, Mass.) and 8 U of Bst 2.0 and 1 ng of Jurkat cell total RNA (Ambion®, Life Technologies, Grand Island, N.Y.) in a one pot reaction where reverse transcription and amplification occurred in the same reaction vessel and at the same temperature. A 25 ul RT-LAMP reaction included 1 ul of Bst 2.0 at 0.12 ug/ul and 0.5 ul RT at 0.1 ug/ul, yielding a mass ratio of RT/Bst 2.0 of 0.24. The double-stranded DNA-specific binding dye SYTO 9 was included at 2 µM for the detection of DNA amplification. The reactions were heated to a reaction temperature of 55° C.–70° C. immediately on a Bio-Rad CFX96™ thermal cycler (Bio-Rad, Hercules, Calif.). As shown in FIG. 1, the rate of amplification of RNA using RT-LAMP is significantly improved when the target RNA is reverse transcribed using the variant V3 RT compared with AMV transcriptase across the temperature range of 55°-70° C.

Example 2

Figure 2:
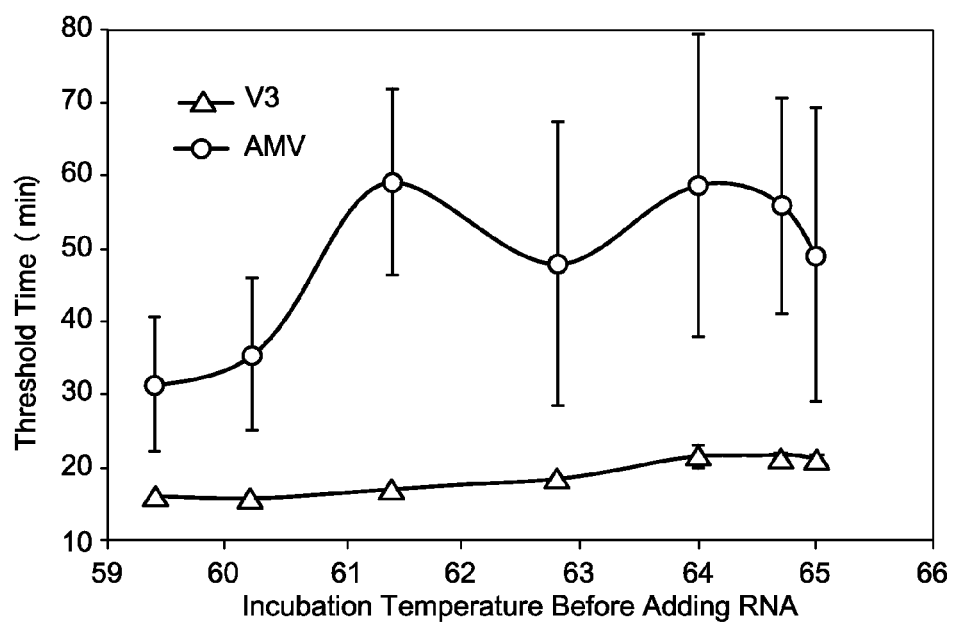
FIG. 2 is a graphical depiction of the relationship of the signal threshold time of LAMP amplification to the RT pre-incubation temperature.
Figure 3:
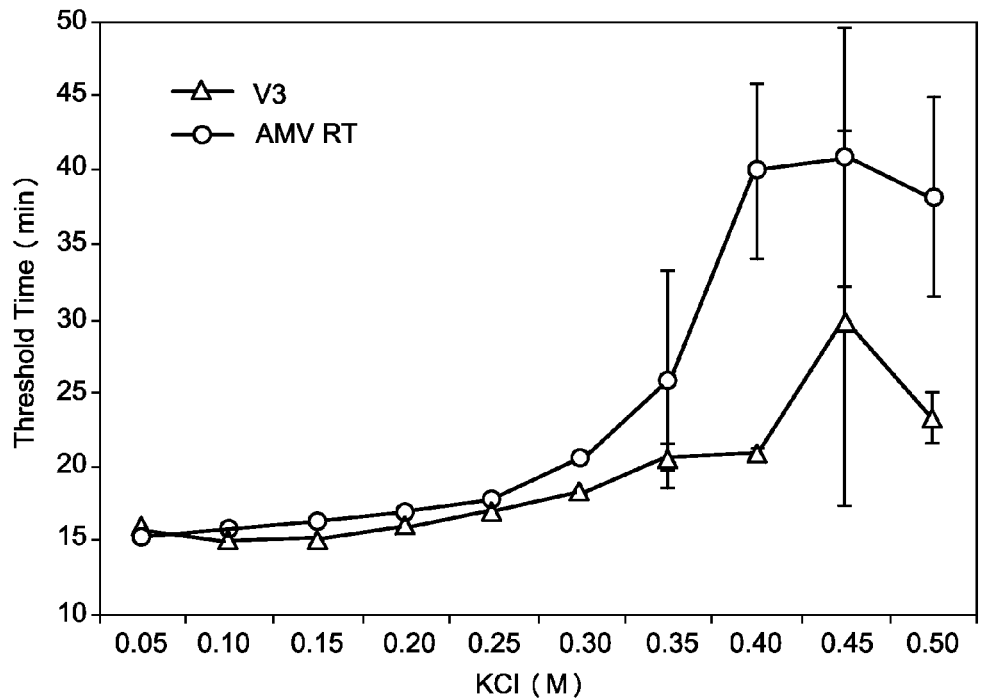
FIG. 3 is a graphical depiction of the relationship of the signal threshold time of LAMP amplification to potassium chloride (KCl) concentration in a two-step RT-LAMP. V3 RT is more resistant to KCl than AMV RT is, particularly at higher KCl concentrations.

Example 2 demonstrates the enhanced thermostability of V3 RT. 50 ng of V3 RT or 5 U of AMV RT were incubated for 2 minutes at 59.4° C.-65° C. in LAMP reactions including Bst 2.0 DNA polymerase, as in Example 1, except for the absence of target RNA. After the incubation the reactions were cooled to 4° C. and then 1 ng of Jurkat cell total RNA was added to start a RT-LAMP reaction at 65° C. As shown in FIG. 2, V3 RT retains activity after 2 minutes pre-incubation at 65° C. prior to addition of RNA substrate, whereas AMV RT lost most of its activity above 60° C.

Example 3

Example 3 demonstrates the enhanced salt tolerance of V3. In the RT step, 50 ng of V3 RT or 5 U AMV RT were incubated at 55° C. for 10 minutes with 10 ng of Jurkat cell total RNA in LAMP reaction buffer, as described in Example 1, excluding Bst 2.0 but adding KCl. After the incubation the reactions were heated to 85° C. to inactivate the RT and cooled to 4° C. In the LAMP step, 1 µl of the RT reaction was then added to a fresh LAMP reaction and incubated at 65° C. V3 RT was significantly more resistant to KCl than AMV RT, particularly at KCl concentrations at or above 0.35M.

Example 4

Example 4 examined the suitability of V3 RT in a carryover prevention involving the incorporation of dUTP in the RT step and in the LAMP amplification step. Contaminant carryover LAMP amplicons were destroyed enzymatically by the Antarctic Thermolabile Uracil-DNA Glycosylase (AT-UDG) (New England Biolabs, Ipswich, Mass.) before amplification.

One-step RT-LAMP was performed with various amounts of Jurkat total RNA as described in FIG. 1, except that 50% of the dTTP was replaced by dUTP. Two sets of reactions (10~7 carryover) also contained 1 µl of $10^{-7}$ dilution of a LAMP reaction generated under the same conditions. One of these two sets also contained 0.5 U AT-UDG (10~7+UDG). A third set had only AT-UDG (0.5 U UDG). Each reaction had 50 ng of V3 RT and 8 U of Bst 2.0. The reaction was prepared on ice and then immediately brought to 65° C. LAMP temperature.

As shown, V3 RT is compatible with the LAMP carryover contamination prevention system. The presence of UDG did not substantially interfere with the activity of V3 RT and dUTP was efficiently used as a substrate during DNA synthesis by V3 RT.

Figure 4:
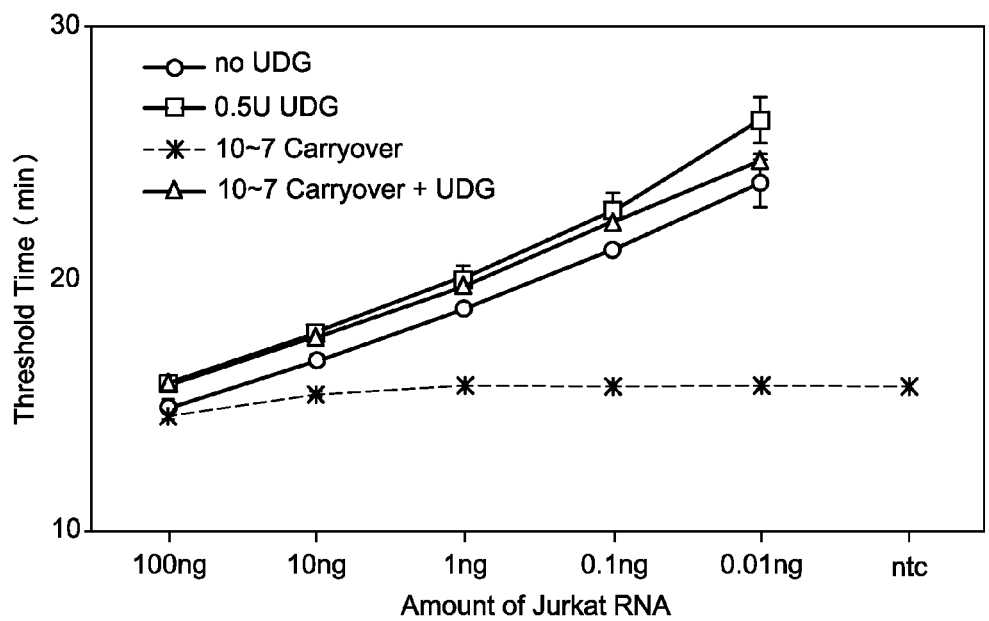
FIG. 4 is a graphical depiction of the relationship of the signal threshold time of LAMP amplification to the amount of template RNA ("Jurkat RNA") in the absence (circles and asterisks) or presence (squares and triangles) of uracil-DNA Glycosylase (UDG) and in the absence (circles and squares) or presence (asterisks and triangles) of contaminating DNA ("carryover"). As shown, V3 RT is effective even in the presence of UDG.

The X-axis in FIG. 4 shows increasing amounts of Jurkat RNA and the Y-axis reflects the threshold time for each reaction. In the absence of carryover but the presence of UDG (square), the RT-LAMP achieved the same detection sensitivity as without UDG (circle), although with a slightly increased reaction time. In the presence of carryover (*), the amplification signal was only from the carryover and quickly reached the threshold time. When both UDG and carryover were added (triangle), the high level of amplification signal was removed and no signal was observed in no template control (ntc) reactions. The amplification signal level varied according to the amount of template RNA as in reactions without carryover. Similar kinetics of carryover prevention were observed with DNA templates, which do not require RT.

Example 5

Figure 5A:
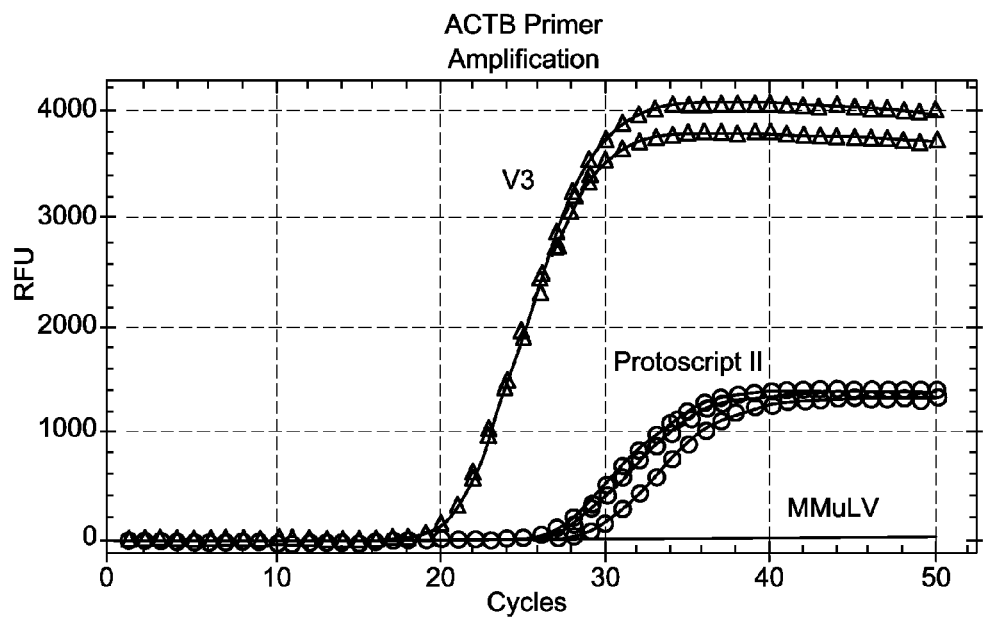
FIG. 5A-B is a graphical depiction of amplification efficiency in quantitative RT-PCR for three RTs: V3, ProtoScript® II (New England Biolabs, Ipswich, Mass.) and MMuLV-RT.
Figure 5B:
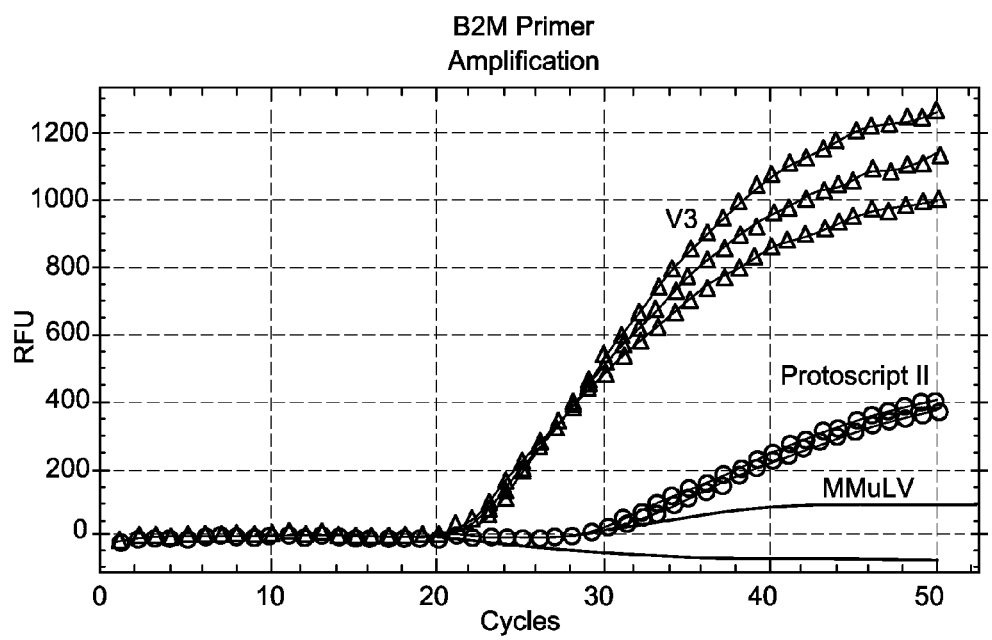

Example 5 demonstrated the enhanced efficiency of V3 in RT-PCR. V3 RT, ProtoScript II and MMuLV RT in RT-PCR. qRT-PCR was performed using primer pairs ACTB (ACTB-F:CTGGAACGGTGAAGGTGACA (SEQ ID NO:13); ACTB-RR, AAGGGACTTCCTGTAACAACGCA (SEQ ID NO:14)) targeting the Actin B gene or B2M (B2M-F: TGCTGTCTCCATGTTTGATGTATCT (SEQ ID NO:15); B2M-R: TCTCTGCTCCCCACCTCTAAGT (SEQ ID NO:16) targeting the B2M gene with 10 ng of Jurkat cell total RNA. The qRT-PCR performed in 25 µl of 1× ThermoPol® buffer (New England Biolabs, Ipswich, Mass.) supplement with MgSO4 to a final of 3 mM Mg++, 400 uM each dNTP, 0.625 U Hot Start Taq DNA polymerase (New England Biolabs, Ipswich, Mass.), 400 nM each of the forward and reverse primer, 2 µM SYTO 9. For RT, it is either 50 ng of V3 RT, or 100 U ProtoScript II RT (New England Biolabs, Ipswich, Mass.) or 100 U MMuLV RT (New England Biolabs, Ipswich, Mass.). The reaction mix was incubated at 54° C. for 5 minutes and then temperature cycled at 95° C. for 10 seconds, 58° C. for 15 seconds, and 68° C. for 30 seconds. The DNA amplification signal was acquired on a Bio-Rad CFX96 thermal cycler. As shown in FIG. 5A-B, V3 RT generated a robust qRT-PCR signal much more rapidly than did the other enzymes.

What is claimed is:

1. A non-naturally occurring reverse transcriptase comprising an amino acid sequence at least 96% identical to SEQ ID NO:18,
and wherein the amino acid sequence of the reverse transcriptase differs from SEQ ID NO:17 at all of the amino acid positions corresponding to Valine at position 35, Glutamic acid at position 122, Aspartic acid at position 177, Glutamine at position 207, Arginine at position 211, Leucine at position 214, Valine at position 245, Arginine at position 277, Threonine at position 286, Glutamic acid at position 291 Isoleucine at position 293, Glycine at position 359 Alanine at position 371, Threonine at position 376, Lysine at position 390, Lysine at position 431, Asparagine at position 460, Threonine at position 468, Aspartic acid at position 471, Tyrosine at position 483, Leucine at position 491, Glutamine at position 512, Alanine at position 534, and Alanine at position 554.

2. The reverse transcriptase of claim 1, wherein the amino acid sequence is at least 98% identical to SEQ ID NO:18.

3. The reverse transcriptase of claim 1, wherein the amino acid sequence is 100% identical to SEQ ID NO:18.

4. A reverse transcriptase according to claim 1, wherein the reverse transcriptase further comprises a second, heterologous amino acid sequence.

5. An enzyme preparation comprising a reverse transcriptase according to claim 1, wherein the enzyme preparation is substantially free of contaminating nucleic acids.

6. An enzyme preparation comprising a reverse transcriptase according to claim 1 and a detergent.

7. The enzyme preparation of claim 6, wherein the detergent is selected from the group consisting of a non-ionic detergent, a cationic, an anionic detergent, and a zwitterionic detergent.

8. The enzyme preparation according to claim 5, further comprising at least 0.35M KCl.

9. The enzyme preparation according to claim 5, further comprising dUTP.

10. The enzyme preparation according to claim 5, further comprising a target RNA.

11. The enzyme preparation according to claim 10, wherein the target RNA is from a cell.

12. The enzyme preparation according to claim 10, wherein the target RNA further comprises a synthetic RNA adapter.

13. The enzyme preparation according to claim 10, wherein the RNA is the product of two RNA molecules ligated to form a single RNA molecule.

14. The enzyme preparation according to claim 10, further comprising at least two primers.

15. The enzyme preparation of claim 14, wherein at least one primer is attached to a solid support.

16. The enzyme preparation according to claim 14, wherein the primer comprises a first nucleic acid sequence for hybridizing to a target RNA in a sample and a second nucleic acid sequence for encoding information about the target RNA upon amplification of the target RNA.

17. The enzyme preparation according to claim 5, further comprising a DNA-dependent DNA polymerase.

18. The enzyme preparation of claim 17, wherein the molecular ratio of the reverse transcriptase and the DNA-dependent DNA polymerase is less than 2:1.

19. The enzyme preparation according to claim 5, further comprising a buffer.

20. The enzyme preparation of claim 19, wherein the buffer has a pH between 8.3 and 9.3.

21. A method of reverse transcribing RNA, the method comprising incubating a reaction comprising RNA, the non-naturally occurring reverse transcriptase of claim 1, a buffer, and deoxyribonucleotides, to reverse transcribe the RNA to produce a complementary strand of DNA.

22. The method of claim 21, wherein the method shows improved activity, salt tolerance, thermostability, and/or dUTP tolerance as compared to a method comprising exposing the same RNA to AMV reverse transcriptase or MuMLV reverse transcriptase under the same conditions.

23. The method according to claim 21, further comprising purifying the RNA prior to the incubation step.

24. The method according to claim 23, wherein the purifying comprises hybridizing the RNA to a complementary oligonucleotide attached to a solid support.

25. The method according to claim 21, further comprising exposing the complementary strand of DNA to a DNA-dependent DNA polymerase in the presence of primers, deoxyribonucleotides, and buffer.

26. The method of claim 25, wherein the DNA-dependent DNA polymerase amplifies the DNA by loop-mediated isothermal amplification.

27. A kit comprising the reverse transcriptase according to claim 1 and, as one or more separate components, at least one element selected from the group consisting of: a buffer, a nucleic acid, deoxyribonucleotides, potassium chloride, magnesium sulfate, ammonium sulfate, a nucleic acid binding dye, a DNA-dependent DNA polymerase, and a uracil-DNA glycosylase.

28. A method for one-step RT-PCR, said method comprising:
   (a) mixing an RNA template with a composition comprising the reverse transcriptase according to claim 1 and one or more DNA polymerases;
   (b) incubating the mixture under conditions sufficient to amplify a DNA molecule complementary to all or a portion of the RNA template.

* * * * *

SEQUENCE LISTING

```
<160> NUMBER OF SEQ ID NOS: 18

<210> SEQ ID NO 1
<211> LENGTH: 561
<212> TYPE: PRT
<213> ORGANISM: Artificial Sequence
<220> FEATURE:
<223> OTHER INFORMATION: Syntheitic construct

<400> SEQUENCE: 1

Met Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
            20                  25                  30

Lys Ala Leu Val Glu Ile Cys Thr Glu Met Glu Lys Glu Gly Lys Ile
        35                  40                  45

Ser Lys Ile Gly Pro Glu Asn Pro Tyr Asn Thr Pro Val Phe Ala Ile
    50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
            100                 105                 110
```

```
Gly Asp Ala Tyr Phe Ser Val Pro Leu Asp Glu Asp Phe Arg Lys Tyr
            115                 120                 125

Thr Ala Phe Thr Ile Pro Ser Ile Asn Asn Glu Thr Pro Gly Ile Arg
130                 135                 140

Tyr Gln Tyr Asn Val Leu Pro Gln Gly Trp Lys Gly Ser Pro Ala Ile
145                 150                 155                 160

Phe Gln Ser Ser Met Thr Lys Ile Leu Glu Pro Phe Arg Lys Gln Asn
                165                 170                 175

Pro Asp Ile Val Ile Tyr Gln Tyr Met Asp Asp Leu Tyr Val Gly Ser
            180                 185                 190

Asp Leu Glu Ile Gly Gln His Arg Thr Lys Ile Glu Glu Leu Arg Gln
        195                 200                 205

His Leu Leu Arg Trp Gly Leu Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Val Leu Pro Glu Lys Asp Ser Trp Thr Val Asn
                245                 250                 255

Asp Ile Gln Lys Leu Val Gly Lys Leu Asn Trp Ala Ser Gln Ile Tyr
            260                 265                 270

Pro Gly Ile Lys Val Arg Gln Leu Cys Lys Leu Leu Arg Gly Thr Lys
        275                 280                 285

Ala Leu Thr Glu Val Ile Pro Leu Thr Glu Glu Ala Glu Leu Glu Leu
    290                 295                 300

Ala Glu Asn Arg Glu Ile Leu Lys Glu Pro Val His Gly Val Tyr Tyr
305                 310                 315                 320

Asp Pro Ser Lys Asp Leu Ile Ala Glu Ile Gln Lys Gln Gly Gln Gly
                325                 330                 335

Gln Trp Thr Tyr Gln Ile Tyr Gln Glu Pro Phe Lys Asn Leu Lys Thr
            340                 345                 350

Gly Lys Tyr Ala Arg Met Arg Gly Ala His Thr Asn Asp Val Lys Gln
        355                 360                 365

Leu Thr Glu Ala Val Gln Lys Ile Thr Thr Glu Ser Ile Val Ile Trp
    370                 375                 380

Gly Lys Thr Pro Lys Phe Lys Leu Pro Ile Gln Lys Glu Thr Trp Glu
385                 390                 395                 400

Thr Trp Trp Thr Glu Tyr Trp Gln Ala Thr Trp Ile Pro Glu Trp Glu
                405                 410                 415

Phe Val Asn Thr Pro Pro Leu Val Lys Leu Trp Tyr Gln Leu Glu Lys
            420                 425                 430

Glu Pro Ile Val Gly Ala Glu Thr Phe Tyr Val Asp Gly Ala Ala Asn
        435                 440                 445

Arg Glu Thr Lys Leu Gly Lys Ala Gly Tyr Val Thr Asn Arg Gly Arg
    450                 455                 460

Gln Lys Val Val Thr Leu Thr Asp Thr Thr Asn Gln Lys Thr Glu Leu
465                 470                 475                 480

Gln Ala Ile Tyr Leu Ala Leu Gln Asp Ser Gly Leu Glu Val Asn Ile
                485                 490                 495

Val Thr Asp Ser Gln Tyr Ala Leu Gly Ile Ile Gln Ala Gln Pro Asp
            500                 505                 510

Gln Ser Glu Ser Glu Leu Val Asn Gln Ile Ile Glu Gln Leu Ile Lys
        515                 520                 525

Lys Glu Lys Val Tyr Leu Ala Trp Val Pro Ala His Lys Gly Ile Gly
```

```
                530                 535                 540
Gly Asn Glu Gln Val Asp Lys Leu Val Ser Ala Gly Ile Arg Lys Val
545                 550                 555                 560

Leu

<210> SEQ ID NO 2
<211> LENGTH: 561
<212> TYPE: PRT
<213> ORGANISM: Artificial Sequence
<220> FEATURE:
<223> OTHER INFORMATION: Synthetic construct

<400> SEQUENCE: 2

Met Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
                20                  25                  30

Lys Ala Leu Thr Glu Ile Cys Thr Glu Met Glu Lys Glu Gly Lys Ile
            35                  40                  45

Ser Lys Ile Gly Pro Glu Asn Pro Tyr Asn Thr Pro Val Phe Ala Ile
        50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
                100                 105                 110

Gly Asp Ala Tyr Phe Ser Val Pro Leu Asp Lys Asp Phe Arg Lys Tyr
            115                 120                 125

Thr Ala Phe Thr Ile Pro Ser Ile Asn Asn Glu Thr Pro Gly Ile Arg
        130                 135                 140

Tyr Gln Tyr Asn Val Leu Pro Gln Gly Trp Lys Gly Ser Pro Ala Ile
145                 150                 155                 160

Phe Gln Ser Ser Met Thr Lys Ile Leu Glu Pro Phe Arg Lys Gln Asn
                165                 170                 175

Pro Glu Ile Val Ile Tyr Gln Tyr Met Asp Asp Leu Tyr Val Gly Ser
            180                 185                 190

Asp Leu Glu Ile Gly Gln His Arg Thr Lys Ile Glu Glu Leu Arg Glu
        195                 200                 205

His Leu Leu Lys Trp Gly Phe Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Gln Leu Pro Glu Lys Asp Ser Trp Thr Val Asn
                245                 250                 255

Asp Ile Gln Lys Leu Val Gly Lys Leu Asn Trp Ala Ser Gln Ile Tyr
            260                 265                 270

Pro Gly Ile Lys Val Lys Gln Leu Cys Lys Leu Leu Arg Gly Ala Lys
        275                 280                 285

Ala Leu Thr Asp Val Val Pro Leu Thr Glu Glu Ala Glu Leu Glu Leu
    290                 295                 300

Ala Glu Asn Arg Glu Ile Leu Lys Glu Pro Val His Gly Val Tyr Tyr
305                 310                 315                 320

Asp Pro Ser Lys Asp Leu Ile Ala Glu Ile Gln Lys Gln Gly Gln Gly
                325                 330                 335
```

Gln Trp Thr Tyr Gln Ile Tyr Gln Glu Pro Phe Lys Asn Leu Lys Thr
                340                 345                 350

Gly Lys Tyr Ala Lys Met Arg Ser Ala His Thr Asn Asp Val Lys Gln
            355                 360                 365

Leu Thr Glu Val Val Gln Lys Ile Ala Thr Glu Ser Ile Val Ile Trp
370                 375                 380

Gly Lys Thr Pro Lys Phe Arg Leu Pro Ile Gln Lys Glu Thr Trp Glu
385                 390                 395                 400

Thr Trp Trp Thr Glu Tyr Trp Gln Ala Thr Trp Ile Pro Glu Trp Glu
                405                 410                 415

Phe Val Asn Thr Pro Pro Leu Val Lys Leu Trp Tyr Gln Leu Glu Thr
                420                 425                 430

Glu Pro Ile Val Gly Ala Glu Thr Phe Tyr Val Asp Gly Ala Ala Asn
            435                 440                 445

Arg Glu Thr Lys Leu Gly Lys Ala Gly Tyr Val Thr Asp Arg Gly Arg
        450                 455                 460

Gln Lys Val Val Ser Leu Thr Glu Thr Thr Asn Gln Lys Thr Glu Leu
465                 470                 475                 480

Gln Ala Ile Gln Leu Ala Leu Gln Asp Ser Gly Ser Glu Val Asn Ile
                485                 490                 495

Val Thr Asp Ser Gln Tyr Ala Leu Gly Ile Ile Gln Ala Gln Pro Asp
                500                 505                 510

Lys Ser Glu Ser Glu Leu Val Asn Gln Ile Ile Glu Gln Leu Ile Lys
            515                 520                 525

Lys Glu Lys Val Tyr Leu Ser Trp Val Pro Ala His Lys Gly Ile Gly
        530                 535                 540

Gly Asn Glu Gln Val Asp Lys Leu Val Ser Ser Gly Ile Arg Lys Val
545                 550                 555                 560

Leu

<210> SEQ ID NO 3
<211> LENGTH: 561
<212> TYPE: PRT
<213> ORGANISM: Artificial Sequence
<220> FEATURE:
<223> OTHER INFORMATION: Synthetic construct

<400> SEQUENCE: 3

Phe Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
            20                  25                  30

Lys Ala Leu Val Glu Ile Cys Thr Glu Met Glu Lys Glu Gly Lys Ile
        35                  40                  45

Ser Lys Ile Gly Pro Glu Asn Pro Tyr Asn Thr Pro Val Phe Ala Ile
    50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
            100                 105                 110

Gly Asp Ala Tyr Phe Ser Val Pro Leu Asp Lys Glu Phe Arg Lys Tyr
        115                 120                 125

```
Thr Ala Phe Thr Ile Pro Ser Ile Asn Asn Glu Thr Pro Arg Ile Arg
    130                 135                 140

Tyr Gln Tyr Asn Val Leu Pro Gln Gly Trp Lys Gly Ser Pro Ala Ile
145                 150                 155                 160

Phe Gln Ser Ser Met Thr Lys Ile Leu Glu Pro Phe Lys Lys Gln Asn
                165                 170                 175

Pro Glu Ile Val Ile Tyr Gln Tyr Met Asp Asp Leu Tyr Val Gly Ser
                180                 185                 190

Asp Leu Glu Ile Gly Gln His Arg Ile Lys Ile Glu Glu Leu Arg Glu
            195                 200                 205

His Leu Leu Lys Trp Gly Phe Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Val Leu Pro Glu Lys Asp Ser Trp Thr Val Asn
                245                 250                 255

Asp Ile Gln Lys Leu Val Gly Lys Leu Asn Trp Ala Ser Gln Ile Tyr
            260                 265                 270

Ala Gly Ile Lys Val Lys Gln Leu Cys Lys Leu Leu Arg Gly Thr Lys
        275                 280                 285

Ala Leu Thr Glu Val Val Gln Leu Thr Lys Glu Ala Glu Leu Glu Leu
    290                 295                 300

Ala Glu Asn Arg Glu Ile Leu Lys Glu Pro Val His Gly Val Tyr Tyr
305                 310                 315                 320

Asp Pro Ser Lys Asp Leu Ile Ala Glu Ile Gln Lys Gln Gly Gln Gly
                325                 330                 335

Gln Trp Thr Tyr Gln Ile Tyr Gln Glu Pro Phe Lys Asn Leu Lys Thr
            340                 345                 350

Gly Lys Tyr Ala Arg Met Arg Gly Ala His Thr Asn Asp Val Lys Gln
        355                 360                 365

Leu Thr Glu Ala Val Gln Lys Val Ala Thr Glu Ser Ile Val Ile Trp
    370                 375                 380

Gly Lys Thr Pro Lys Phe Lys Leu Pro Ile Gln Lys Glu Thr Trp Glu
385                 390                 395                 400

Ala Trp Trp Thr Glu Tyr Trp Gln Ala Thr Trp Ile Pro Glu Trp Glu
                405                 410                 415

Phe Val Asn Thr Pro Pro Leu Val Lys Leu Trp Tyr Gln Leu Glu Lys
            420                 425                 430

Glu Pro Ile Ile Gly Ala Glu Thr Phe Tyr Val Asp Gly Ala Ala Asn
        435                 440                 445

Arg Glu Thr Lys Leu Gly Lys Ala Gly Tyr Val Thr Asp Arg Gly Arg
    450                 455                 460

Gln Lys Val Val Ser Leu Thr Asp Thr Thr Asn Gln Lys Thr Glu Leu
465                 470                 475                 480

Gln Ala Ile His Leu Ala Leu Gln Asp Ser Gly Leu Glu Val Asn Ile
                485                 490                 495

Val Thr Asp Ser Gln Tyr Ala Leu Gly Ile Ile Gln Ala Gln Pro Asp
            500                 505                 510

Lys Ser Glu Ser Glu Leu Val Ser Gln Ile Ile Glu Gln Leu Ile Lys
        515                 520                 525

Lys Glu Lys Val Tyr Leu Ala Trp Val Pro Ala His Lys Gly Ile Gly
    530                 535                 540

Gly Asn Glu Gln Val Asp Arg Leu Val Ser Thr Gly Ile Arg Lys Val
```

```
                545                 550                 555                 560
Leu

<210> SEQ ID NO 4
<211> LENGTH: 561
<212> TYPE: PRT
<213> ORGANISM: Artificial Sequence
<220> FEATURE:
<223> OTHER INFORMATION: Synthetic construct

<400> SEQUENCE: 4

Phe Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Lys Ile
            20                  25                  30

Glu Ala Leu Arg Glu Ile Cys Thr Glu Met Glu Lys Glu Gly Lys Ile
        35                  40                  45

Ser Arg Ile Gly Pro Glu Asn Pro Tyr Asn Thr Pro Ile Phe Ala Ile
    50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Gln Lys Ser Val Thr Val Leu Asp Val
            100                 105                 110

Gly Asp Ala Tyr Phe Ser Cys Pro Leu Asp Lys Asp Phe Arg Lys Tyr
            115                 120                 125

Thr Ala Phe Thr Ile Pro Ser Ile Asn Asn Glu Thr Pro Gly Ile Arg
    130                 135                 140

Tyr Gln Tyr Asn Val Leu Pro Gln Gly Trp Lys Gly Ser Pro Ala Ile
145                 150                 155                 160

Phe Gln Ser Thr Met Thr Lys Ile Leu Glu Pro Phe Arg Glu Lys His
                165                 170                 175

Pro Glu Ile Ile Ile Tyr Gln Tyr Met Asp Asp Leu Tyr Val Gly Ser
            180                 185                 190

Asp Leu Glu Leu Ala Gln His Arg Glu Ala Val Glu Asp Leu Arg Asp
        195                 200                 205

His Leu Leu Lys Trp Gly Phe Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Lys Leu Pro Glu Lys Asp Val Trp Thr Val Asn
                245                 250                 255

Asp Ile Gln Lys Leu Val Gly Lys Leu Asn Trp Ala Ser Gln Ile Tyr
            260                 265                 270

Pro Gly Ile Arg Val Lys Gln Leu Cys Lys Leu Ile Arg Gly Thr Lys
        275                 280                 285

Ala Leu Thr Glu Val Val Asn Phe Thr Glu Glu Ala Glu Leu Glu Leu
    290                 295                 300

Ala Glu Asn Arg Glu Ile Leu Lys Glu Pro Leu His Gly Val Tyr Tyr
305                 310                 315                 320

Asp Pro Gly Lys Glu Leu Val Ala Glu Ile Gln Lys Gln Gly Gln Gly
                325                 330                 335

Gln Trp Thr Tyr Gln Ile Tyr Gln Glu Leu His Lys Asn Leu Lys Thr
            340                 345                 350
```

```
Gly Lys Tyr Ala Lys Met Arg Ser Ala His Thr Asn Asp Ile Lys Gln
            355                 360                 365

Leu Val Glu Val Val Arg Lys Val Ala Thr Glu Ser Ile Val Ile Trp
    370                 375                 380

Gly Lys Thr Pro Lys Phe Arg Leu Pro Val Gln Lys Glu Val Trp Glu
385                 390                 395                 400

Ala Trp Trp Thr Asp His Trp Gln Ala Thr Trp Ile Pro Glu Trp Glu
                405                 410                 415

Phe Val Asn Thr Pro Pro Leu Val Lys Leu Trp Tyr Gln Leu Glu Thr
                420                 425                 430

Glu Pro Ile Ser Gly Ala Glu Thr Phe Tyr Val Asp Gly Ala Ala Asn
                435                 440                 445

Arg Glu Thr Lys Leu Gly Lys Ala Gly Phe Val Thr Asp Arg Gly Arg
    450                 455                 460

Gln Lys Val Val Ser Ile Ala Asp Thr Thr Asn Gln Lys Ala Glu Leu
465                 470                 475                 480

Gln Ala Ile Leu Met Ala Leu Gln Glu Ser Gly Arg Asp Val Asn Ile
                485                 490                 495

Val Thr Asp Ser Gln Tyr Ala Met Gly Ile Ile His Ser Gln Pro Asp
                500                 505                 510

Lys Ser Glu Ser Glu Leu Val Ser Gln Ile Ile Glu Glu Leu Ile Lys
                515                 520                 525

Lys Glu Arg Val Tyr Leu Ser Trp Val Pro Ala His Lys Gly Ile Gly
    530                 535                 540

Gly Asn Glu Gln Val Asp Lys Leu Val Ser Ser Gly Ile Arg Lys Ile
545                 550                 555                 560

Leu

<210> SEQ ID NO 5
<211> LENGTH: 560
<212> TYPE: PRT
<213> ORGANISM: Artificial Sequence
<220> FEATURE:
<223> OTHER INFORMATION: Synthetic construct

<400> SEQUENCE: 5

Phe Pro Ile Ser Pro Ile Glu Val Val Lys Val Gln Leu Lys Glu Gly
1               5                   10                  15

Met Asp Gly Pro Lys Val Lys Gln Trp Pro Leu Ser Lys Glu Lys Ile
                20                  25                  30

Glu Ala Leu Thr Glu Ile Cys Lys Thr Leu Glu Lys Glu Gly Lys Ile
            35                  40                  45

Ser Ala Val Gly Pro Glu Asn Pro Tyr Asn Thr Pro Ile Phe Ala Ile
        50                  55                  60

Lys Lys Lys Asp Thr Ser Lys Trp Arg Lys Leu Val Asp Phe Arg Glu
65                  70                  75                  80

Leu Asn Lys Arg Thr Gln Asp Phe Trp Glu Leu Gln Leu Gly Ile Pro
                85                  90                  95

His Pro Ala Gly Leu Arg Lys Arg Asn Met Val Thr Val Leu Asp Val
                100                 105                 110

Gly Asp Ala Tyr Phe Ser Ile Pro Leu Asp Pro Asp Phe Arg Lys Tyr
            115                 120                 125

Thr Ala Phe Thr Ile Pro Ser Leu Asn Asn Asn Thr Pro Gly Lys Arg
        130                 135                 140
```

```
Phe Gln Tyr Asn Val Leu Pro Gln Gly Trp Lys Gly Ser Pro Ala Ile
145                 150                 155                 160

Phe Gln Ser Ser Met Thr Lys Ile Leu Asp Pro Phe Arg Lys Glu His
            165                 170                 175

Pro Asp Val Asp Ile Tyr Gln Tyr Met Asp Asp Leu Tyr Ile Gly Ser
                180                 185                 190

Asp Leu Asn Glu Glu His Arg Lys Leu Ile Lys Lys Leu Arg Gln
        195                 200                 205

His Leu Leu Thr Trp Gly Leu Glu Thr Pro Asp Lys Lys Tyr Gln Glu
        210                 215                 220

Lys Pro Pro Phe Met Trp Met Gly Tyr Glu Leu His Pro Asn Lys Trp
225                 230                 235                 240

Thr Val Gln Asn Ile Thr Leu Pro Glu Pro Glu Gln Trp Thr Val Asn
                245                 250                 255

His Ile Gln Lys Leu Val Gly Lys Leu Asn Trp Ala Ser Gln Ile Tyr
            260                 265                 270

His Gly Ile Lys Thr Lys Glu Leu Cys Lys Leu Ile Arg Gly Val Lys
            275                 280                 285

Gly Leu Thr Glu Pro Val Glu Met Thr Arg Glu Ala Glu Leu Glu Leu
290                 295                 300

Glu Glu Asn Lys Gln Ile Leu Lys Glu Lys Val Gln Gly Ala Tyr Tyr
305                 310                 315                 320

Asp Pro Lys Leu Pro Leu Gln Ala Ala Ile Gln Lys Gly Gln Gly
            325                 330                 335

Gln Trp Thr Tyr Gln Ile Tyr Gln Glu Glu Gly Lys Asn Leu Lys Thr
                340                 345                 350

Gly Lys Tyr Ala Lys Ser Pro Gly Thr His Thr Asn Glu Ile Arg Gln
            355                 360                 365

Leu Ala Gly Leu Ile Gln Lys Ile Gly Asn Glu Ser Ile Ile Ile Trp
        370                 375                 380

Gly Ile Val Pro Lys Phe Leu Leu Pro Val Ser Lys Glu Thr Trp Ser
385                 390                 395                 400

Gln Trp Trp Thr Asp Tyr Trp Gln Val Thr Trp Val Pro Glu Trp Glu
                405                 410                 415

Phe Ile Asn Thr Pro Pro Leu Ile Arg Leu Trp Tyr Asn Leu Leu Ser
            420                 425                 430

Asp Pro Ile Pro Glu Ala Glu Thr Phe Tyr Val Asp Gly Ala Ala Asn
            435                 440                 445

Arg Asp Ser Lys Lys Gly Arg Ala Gly Tyr Val Thr Asn Arg Gly Arg
450                 455                 460

Tyr Arg Ser Lys Asp Leu Glu Asn Thr Thr Asn Gln Gln Ala Glu Leu
465                 470                 475                 480

Trp Ala Val Asp Leu Ala Leu Lys Asp Ser Gly Ala Gln Val Asn Ile
            485                 490                 495

Val Thr Asp Ser Gln Tyr Val Met Gly Val Leu Gln Gly Leu Pro Asp
                500                 505                 510

Gln Ser Asp Ser Pro Ile Val Glu Gln Ile Ile Gln Lys Leu Thr Gln
            515                 520                 525

Lys Thr Ala Ile Tyr Leu Ala Trp Val Pro Ala His Lys Gly Ile Gly
            530                 535                 540

Gly Asn Glu Glu Val Asp Lys Leu Val Ser Lys Asn Ile Arg Lys Ile
545                 550                 555                 560
```

```
<210> SEQ ID NO 6
<211> LENGTH: 440
<212> TYPE: PRT
<213> ORGANISM: Artificial Sequence
<220> FEATURE:
<223> OTHER INFORMATION: Synthetic construct

<400> SEQUENCE: 6

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Thr Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Lys Asp Phe Arg Lys Tyr Thr
            115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Glu Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Glu His
        195                 200                 205

Leu Leu Lys Trp Gly Phe Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Gln Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Lys Gln Leu Cys Lys Leu Leu Arg Gly Ala Lys Ala
        275                 280                 285

Leu Thr Asp Val Val Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Ser Ala His Thr Asn Asp Val Lys Gln Leu
        355                 360                 365

Thr Glu Val Val Gln Lys Ile Ala Thr Glu Ser Ile Val Ile Trp Gly
```

```
                    370                 375                 380
Lys Thr Pro Lys Phe Arg Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Thr Glu
                420                 425                 430

Pro Ile Val Gly Ala Glu Thr Phe
            435                 440
```

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
agtaccccat cgagcacg        18

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
agcctggata gcaacgtaca        20

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
gagccacacg cagctcattg tatcaccaac tgggacgaca        40

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
ctgaacccca aggccaaccg gctggggtgt tgaaggtc        38

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tgtggtgcca gattttctcc a        21

<210> SEQ ID NO 12
<211> LENGTH: 23
<212> TYPE: DNA
<213> ORGANISM: Artificial Sequence

```
<220> FEATURE:
<223> OTHER INFORMATION: Primer

<400> SEQUENCE: 12
cgagaagatg acccagatca tgt                                          23

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctggaacggt gaaggtgaca                                              20

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
aagggacttc ctgtaacaac gca                                          23

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
tgctgtctcc atgtttgatg tatct                                        25

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tctctgctcc ccacctctaa gt                                           22

<210> SEQ ID NO 17
<211> LENGTH: 560
<212> TYPE: PRT
<213> ORGANISM: Artificial Sequence
<220> FEATURE:
<223> OTHER INFORMATION: Synthetic construct

<400> SEQUENCE: 17
```

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
                20                  25                  30

Ala Leu Val Glu Ile Cys Thr Glu Met Glu Lys Glu Gly Lys Ile Ser
            35                  40                  45

Lys Ile Gly Pro Glu Asn Pro Tyr Asn Thr Pro Val Phe Ala Ile Lys
        50                  55                  60

Lys Lys Asp Ser Thr Lys Trp Arg Lys Leu Val Asp Phe Arg Glu Leu
65                  70                  75                  80

-continued

```
Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
                115                 120                 125

Ala Phe Thr Ile Pro Ser Ile Asn Asn Glu Thr Pro Gly Ile Arg Tyr
130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
                180                 185                 190

Leu Glu Ile Gly Gln His Arg Thr Lys Ile Glu Glu Leu Arg Gln His
                195                 200                 205

Leu Leu Arg Trp Gly Leu Thr Thr Pro Asp Lys Lys His Gln Lys Glu
        210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
                260                 265                 270

Gly Ile Lys Val Arg Gln Leu Cys Lys Leu Leu Arg Gly Thr Lys Ala
                275                 280                 285

Leu Thr Glu Val Ile Pro Leu Thr Glu Glu Ala Glu Leu Glu Leu Ala
        290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
                340                 345                 350

Lys Tyr Ala Arg Met Arg Gly Ala His Thr Asn Asp Val Lys Gln Leu
                355                 360                 365

Thr Glu Ala Val Gln Lys Ile Thr Thr Glu Ser Ile Val Ile Trp Gly
        370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe Tyr Val Asp Gly Ala Ala Asn Arg
                435                 440                 445

Glu Thr Lys Leu Gly Lys Ala Gly Tyr Val Thr Asn Arg Gly Arg Gln
        450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495
```

```
Thr Asp Ser Gln Tyr Ala Leu Gly Ile Ile Gln Ala Gln Pro Asp Gln
                500                 505                 510

Ser Glu Ser Glu Leu Val Asn Gln Ile Ile Glu Gln Leu Ile Lys Lys
            515                 520                 525

Glu Lys Val Tyr Leu Ala Trp Val Pro Ala His Lys Gly Ile Gly Gly
        530                 535                 540

Asn Glu Gln Val Asp Lys Leu Val Ser Ala Gly Ile Arg Lys Val Leu
545                 550                 555                 560

<210> SEQ ID NO 18
<211> LENGTH: 560
<212> TYPE: PRT
<213> ORGANISM: Artificial Sequence
<220> FEATURE:
<223> OTHER INFORMATION: Synthetic construct

<400> SEQUENCE: 18

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Thr Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Lys Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Glu Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Glu His
        195                 200                 205

Leu Leu Lys Trp Gly Phe Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Gln Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Lys Gln Leu Cys Lys Leu Leu Arg Gly Ala Lys Ala
        275                 280                 285

Leu Thr Asp Val Val Pro Leu Thr Glu Glu Ala Glu Leu Glu Leu Ala
    290                 295                 300
```

-continued

```
Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
                340                 345                 350

Lys Tyr Ala Lys Met Arg Ser Ala His Thr Asn Asp Val Lys Gln Leu
                355                 360                 365

Thr Glu Val Val Gln Lys Ile Ala Thr Glu Ser Ile Val Ile Trp Gly
            370                 375                 380

Lys Thr Pro Lys Phe Arg Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Thr Glu
                420                 425                 430

Pro Ile Val Gly Ala Glu Thr Phe Tyr Val Asp Gly Ala Ala Asn Arg
            435                 440                 445

Glu Thr Lys Leu Gly Lys Ala Gly Tyr Val Thr Asp Arg Gly Arg Gln
        450                 455                 460

Lys Val Val Ser Leu Thr Glu Thr Thr Asn Gln Lys Thr Glu Leu Gln
465                 470                 475                 480

Ala Ile Gln Leu Ala Leu Gln Asp Ser Gly Ser Glu Val Asn Ile Val
                485                 490                 495

Thr Asp Ser Gln Tyr Ala Leu Gly Ile Ile Gln Ala Gln Pro Asp Lys
            500                 505                 510

Ser Glu Ser Glu Leu Val Asn Gln Ile Ile Glu Gln Leu Ile Lys Lys
        515                 520                 525

Glu Lys Val Tyr Leu Ser Trp Val Pro Ala His Lys Gly Ile Gly Gly
    530                 535                 540

Asn Glu Gln Val Asp Lys Leu Val Ser Ser Gly Ile Arg Lys Val Leu
545                 550                 555                 560
```